United States Patent [19]
Daynes et al.

[11] Patent Number: 5,587,369
[45] Date of Patent: *Dec. 24, 1996

[54] METHODS FOR PREVENTING PROGRESSIVE TISSUE NECROSIS, REPERFUSION INJURY, BACTERIAL TRANSLOCATION AND ADULT RESPIRATORY DISTRESS SYNDROME

[75] Inventors: Raymond A. Daynes, Park City; Barbara A. Araneo, Salt Lake City, both of Utah

[73] Assignee: University of Utah Research Foundation, Salt Lake City, Utah

[ * ] Notice: The term of this patent shall not extend beyond the expiration date of Pat. No. 5,489,581.

[21] Appl. No.: 480,744

[22] Filed: Jun. 7, 1995

Related U.S. Application Data

[60] Continuation-in-part of Ser. No. 446,569, May 19, 1995, Pat. No. 5,489,581, which is a division of Ser. No. 284,688, Aug. 9, 1994, Pat. No. 5,532,230, which is a continuation-in-part of Ser. No. 29,422, Mar. 9, 1993, abandoned.

[51] Int. Cl.⁶ ............................................. A61K 31/56
[52] U.S. Cl. ........................ 514/178; 514/177; 514/182
[58] Field of Search ................................. 514/177, 178, 514/182

[56] References Cited

U.S. PATENT DOCUMENTS

| | | | |
|---|---|---|---|
| 4,898,694 | 2/1990 | Schwartz et al. | 260/397.5 |
| 5,001,119 | 3/1991 | Schwartz et al. | 514/177 |
| 5,110,810 | 5/1992 | Eich et al. | 514/178 |
| 5,162,198 | 11/1992 | Eich et al. | 435/2 |
| 5,175,154 | 12/1992 | Schwartz et al. | 514/172 |
| 5,489,581 | 2/1996 | Daynes et al. | 514/170 |

OTHER PUBLICATIONS

Simon, R. H. et al. (1992). "Adult Respiratory Distress Syndrome," Information: Basic Principles and Clinical Correlates, 2nd Ed., J. Gallin et al., Eds., Raven Press (N.Y.), pp. 999–1016.

Meikle, A. W. et al. (1991). "Adrenal Androgen Secretion and Biologic Effects," Endo–crinol. Metab. Clin. N. Am. 29:2, pp. 381–400.

Vedder, N. B. et al. (1990). "Inhibition of Leukocyte Adherence by Anti–CD18 Monoclonal Antibody Attenuates Reperfusion Injury in the Rabbit Ear," Proc. Nat. Acad. Sci. USA 87:2643–2646.

Dolocek, R. (1989). "Endocrine Changes after Burn Trauma—A Review," Keio J. Med. 38(3):262–276.

Gordon, G. et al. (1987). "Modulation of Growth, Differentiation and Carcinogenesis by Dehydroepiandrosterone," Adv. Enz. Regul. 26:355–378.

Erlich, H. P. (1984). "Anti–inflammatory Drugs in the Vascular Response to Burn Injury," J. Trauma 24(4):311–317.

Robson, M. C. (1990). "Increasing Dermal Perfusion after Burning by Decreasing Thromboxane Production," J. Trauma 20(9):722–725.

Robson, M. C. (1978). "The Effect of Prostaglandins on the Dermal Microcirculation After Burning, and the Inhibition of the Effect by Specific Pharmcological Agents," Annual Meeting of the American Society of Plastic and Reconstructive Surgeons, Hollywood, Florida, Nov. 8, 1978.

Primary Examiner—Raymond Henley, III
Attorney, Agent, or Firm—Venable, Baetjer, Howard & Civiletti, LLP

[57] ABSTRACT

The present invention is directed to a method for preventing or reducing ischemia following injury, such as reperfusion injury following ischemia, cellular damage associated with ischemic episodes, such as infarctions or traumatic injuries, and thus to prevent or reduce the consequent progressive necrosis of tissue associated with such ischemia. This effect is achieved by administering DHEA, DHEA derivatives or DHEA congeners to a patient as soon as possible after the injury. The present invention is further directed to methods for preventing or reducing bacterial translocation or adult respiratory distress syndrome in a patient. Similarly, bacterial translocation and adult respiratory distress syndrome are prevented or reduced by administering DHEA, DHEA derivatives or DHEA congeners to a patient.

13 Claims, 9 Drawing Sheets

METHODS FOR PREVENTING PROGRESSIVE TISSUE NECROSIS, REPERFUSION INJURY, BACTERIAL TRANSLOCATION AND ADULT RESPIRATORY DISTRESS SYNDROME

This invention was made with Government support under Grant N00014-92-J-1612 awarded by the Department of the Navy. The Government has certain rights in the invention.

CROSS REFERENCE TO RELATED APPLICATIONS

This application is a continuation-in-part of application Ser. No. 08/446,569, filed May 19, 1995, now U.S. Pat. No. 5,489,581, which in turn is a divisional of application Ser. No. 08/284,668, filed 9 Aug. 1994, now U.S. Pat. No. 5,532,230 which in turn is a continuation-in-part of application Ser. No. 08/029,422, filed 9 Mar. 1993, now abandoned the specification of each is incorporated herein.

BACKGROUND OF THE INVENTION

The present invention is related to a method for preventing or reducing the effects of ischemia. The ischemia may be associated with injury, such as occurs as a result of infarctions, thermal injury (burns), surgical trauma, accidental trauma and the like. The ischemia may also precede reperfusion injury. The invention is also related to methods for preventing or reducing bacterial translocation and adult respiratory distress syndrome. In accordance with the present invention, these conditions are prevented by administering dehydroepiandrosterone (DHEA) or DHEA derivatives.

The publications and other materials used herein to illuminate the background of the invention, and in particular cases, to provide additional details respecting the practice, are incorporated by reference, and for convenience are numerically referenced in the following text and respectively grouped in the appended bibliography.

It has been recognized that the maintenance of vascular integrity is an important response to injury. Complex hemostatic mechanisms of coagulation, platelet function and fibrinolysis exist to minimize adverse consequences of vascular injury and to accelerate vascular repair. Vascular endothelial and smooth muscle cells actively maintain vessel wall thromboresistance by expressing several antithrombotic properties. When perturbed or injured, vascular cells express thrombogenic properties. The hemostatic properties of normal and perturbed vascular cells has been reviewed by Rodgers (1).

Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood. Ischemia is probably the most important cause of coagulative necrosis in human disease. A substantial body of evidence claims that a significant proportion of the injury associated with ischemia is a consequence of the events associated with reperfusion of ischemic tissues, hence the term reperfusion injury. To place reperfusion injury into a clinical perspective, there are three different degrees of cell injury, depending on the duration of ischemia:

(1) With short periods of ischemia, reperfusion (and resupply of oxygen) completely restores the structural and functional integrity of the cell. Whatever degree of injury the cells have incurred can be completely reversed upon reoxygenation. For example, changes in cellular membrane potential, metabolism and ultrastructure are short-lived if the circulation is rapidly restored.

(2) With longer periods of ischemia, reperfusion is not associated with the restoration of cell structure and function, but rather with deterioration and death of cells. The response to reoxygenation in this case is rapid and intense inflammation.

(3) Lethal cell injury may develop during prolonged periods of ischemia, where reperfusion is not a factor.

The reversibility of cell injury as a consequence of ischemia is determined not only by the type and duration of the injury, but also by the cell target. Neurons exhibit very high sensitivity to ischemia, whereas myocardial, pulmonary, hepatic and renal tissues are intermediate in sensitivity. Fibroblasts, epidermis and skeletal muscle have the lowest susceptibility to ischemic injury, requiring several hours without blood supply to develop irreversible damage.

The proximity of the endothelium to circulating leukocytes makes it an important early target for neutrophil adherence and subsequent damage to vascular and parenchymal tissue. Interaction of activated endothelial cells and neutrophils is an immediate early, and necessary, event in ischemia/reperfusion injury (2, 3). The adhesive properties of endothelium are rapidly induced by the influx of oxygenated blood. In response to oxygen, endothelial cells become activated to produce several products, including leukotriene B4 (LTB4), platelet activating factor (PAF) and P-selectin. Leukotriene B4 is a potent neutrophil chemotactic agent (4, 5). Upon activation of the endothelial cells, P-selectin is rapidly translocated from intracellular organelles to the plasma membrane, where it acts to tether circulating neutrophils and stabilize them for activation by endothelial-bound PAF (platelet activating factor), enddothelium-derived cytokines and other biologically active mediators (6). Thus, the physiologic interaction between the activated endothelium and the activated neutrophil is recognized as a critical and immediate early event in reperfusion injury of organs and tissues. Other cellular and biochemical mediators of inflammation injury such as platelets, the complement cascade, and the coagulation system are also important, but come into play much later in the cascade, in a process called coagulative necrosis. Finally, monocytes, macrophages, fibroblasts and smooth muscle cell infiltration are responsible for reconstruction and replacement of dead tissue with new, vital tissue, a process called wound healing.

A popular theory postulates a role for partially reduced, and thus activated, oxygen species in the initiation of membrane damage in reperfusion injury. Present evidence indicates that activated oxygen (superoxide, peroxide, hydroxyl radicals) is formed during ischemic episodes and that reactive oxygen species injure ischemic cells. Toxic oxygen species are generated not during the period of ischemia itself, but rather on restoration of blood flow, or reperfusion. Two sources of activated oxygen species have been implicated as early events in reperfusion injury, those produced intracellularly by the xanthine oxidase pathway and those which can be transported to the extracellular environment by activated neutrophils (2, 3, 7–9).

In the xanthine oxidase-dependent pathway, purines derived from the catabolism of ATP during the ischemic period provide substrates for the activity of xanthine oxidase, which requires oxygen in catalyzing the formation of uric acid. Activated oxygen species are byproducts of this reaction. The species of oxygen radicals derived from the xanthine oxidase pathway are $O_2^-$ (superoxide with one electron) and $H_2O_2$ (hydrogen peroxide with two unpaired electrons). Superoxides are generated within the cytosol by xanthine oxidase (located in the cytosol). The superoxides are then catabolized to peroxides within mitochondria by superoxide dismutase. The peroxides are further converted to water either by glutathione peroxidase, in the cytosol, or by catalase in peroxisomes. Both glutathione peroxidase and catalase comprise the antioxidant defense mechanism of most cells. The major evidence for this hypothesis rests on the ability of allopurinol, an inhibitor of xanthine oxidase, to protect against reperfusion injury in experimental models.

In the NADPH-dependent pathway, NADPH oxidase is activated to generate superoxides through reduction of molecular oxygen at the plasma membrane. The superoxides are reduced to hydrogen peroxide by superoxide dismutase at the plasma membrane or within phagolysosomes. Finally, hydrogen peroxide within phagolysosomes can be reduced in the presence of superoxides or ferrous iron to hydroxyl radicals. A third form of oxygen metabolite is mediated by myloperoxidase in the presence of chlorine to reduce hydrogen peroxide to hypochlorous acid.

The hydroxyl radical is an extremely reactive species. Mitochondrial membranes offer a number of suitable substrates for attack by $OH^-$ radicals. The end result is irreversible damage to mitochondria, perpetuated by a massive influx of $Ca^{2+}$ ions. Another probable cause of cell death by hydroxyl radicals is through peroxidation of phospholipids in the plasma membrane. Unsaturated fatty acids are highly susceptible targets of hydroxyl radicals. By removing a hydrogen atom from fatty acids of cell membrane phospholipids, a free lipid radical is formed. These lipid radicals function like hydroxyl radicals to form other lipid peroxide radicals. The destruction of unsaturated fatty acids of phospholipids leads to a loss in membrane fluidity and cell death. Some investigators believe that the effects of oxidative stress cause programmed cell death in a variety of cell types.

Infarctions and traumatic injury involve many tissues, including vascular tissue. One response following traumatic injury is to shut down blood supply to the injured tissue. A purpose of this response is to protect the patient from the entry of infectious agents into the body. The severe reduction in blood supply is a main factor leading to progressive ischemia at the region of the traumatic injury. With progressive ischemia, tissue necrosis extends beyond the directly affected tissue to include surrounding unaffected tissue. This progressive ischemia plays an important role in defining the ultimate tissue pathology observed in humans as a consequence of the traumatic injury. For example, see Robson et al. (10).

One form of traumatic injury which has received a great deal of attention is thermal injury or burns. The burn wound represents a non-uniform injury, and the spectrum of injury ranges from tissue which is totally coagulated at the time of injury to tissue which is only minimally injured. Between these two extremes is tissue which is seriously damaged and not immediately destroyed, but which is destined to die. The etiology of the progressive depth of necrosis has been shown to be stasis and thrombosis of blood flow in the dermal vessels, causing ischemia and destruction of epithelial elements. This ischemia occurs for 24–48 hours following the thermal injury (10, 11). Many effects have been seen following a thermal injury, including adhesion of leukocytes to vessel walls, agglutination of red blood cells and liberation of vasoactive and necrotizing substances (11).

It has been established that burn-associated micro-vascular occlusion and ischemia are caused by the time dependent increase in development of microthrombi in the zone of stasis, a condition which eventually leads to a total occlusion of the arterioles and a microcir-culatory standstill. Whereas margination of erythrocytes, granulocytes and platelets on venular walls are all apparent within the first few hours following thermal injury, the formation of platelet microthrombi (occurring approximately 24 hours after surgery) is believed to be responsible for creating the conditions that cause complete and permanent vascular occlusion and tissue destruction (12, 13). The formation of platelet microthrombi appears to provide the cellular basis for expanding the zone of complete occlusion and the ischemic necrosis that advances into the zone of stasis following thermal injury.

Much effort has been made toward improving the care of burns and other traumatic injuries, and many approaches have been proposed toward reducing the progressive ischemia associated with such injuries. The anti-inflammatory agents indomethacin, acetylsalicylic acid and methylprednisone acetate have been shown to preserve dermal perfusion (10). Three thromboxane inhibitors, imidazole, methimazole and dipyridamole, have been shown to prevent vascular changes in the burn wound, allow dermal perfusion and allow other prosta- glandin synthesis, which would circumvent detrimental effects of the anti-inflammatory agents (11). Therapeutic doses of ibuprofen and imidazole were found to prevent dermal vascular occlusion by acting as an antagonist to a plasmin inhibitor (14). The reduction of circulating fibrinogen, shown by administration of ancrod (a pit viper venom), led to preservation of vascular potency at the site of the injury (15). It has also been found that the inhibition of leukocyte-endothelial adherence, shown by using monoclonal anti-bodies, prevents burn extension/progression in the marginal zone of stasis (16).

Bacterial translocation is the process by which indigenous gut flora penetrate the intestinal barrier and invade sterile tissue. Included in this process is the migration of microbial organisms to the draining mesenteric lymph nodes, spleen, liver, blood and in some instances, the lung (17, 18). This phenomenon has been documented in humans following thermal injury (19–21) and ischemia-reperfusion injury (22).

Under normal conditions, the intestinal mucosa is impermeable to potentially harmful materials from the intestinal lumen (17, 22, 23). Current data supports the concept that disruption of the integrity/permeability of the mucosa promotes bacterial translocation, since exposure to stress which produces a host response characterized by cellular damage and necrotic tissue correlates with development of bacterial translocation (23). The clinically important repercussions of bacterial translocation are sepsis and multi-system organ failure (22–24). The incidence of sepsis and disseminated organ involvement following stress is greatest among patients that also exhibit compromised immune defenses (22, 23), such as observed in thermally injured individuals (24, 25). Thus, in response to stress, some patients demonstrate bacterial translo-cation in the absence of severe consequences. The patients in this category are those who have retained intact immune defenses (22–24). Because of the well known modulation of the host immune defenses following severe burn, bacterial translocation is one of the more serious consequences of thermal injury in humans (24, 25).

Experimental models of bacterial translocation have noted that irreversible cellular injury of the gut may require up to 24 hours post-thermal injury and 48 hours to visualize histological changes in gut vascular tissue (21, 26). These experimental systems have been useful in defining the pharmacologic mediators which appear to formulate a cascade of effector molecules responsible for tissue necrosis. In addition to the role played by catecholamines, oxygen-free radicals and endotoxin, factors such as interferon alpha, interleu- kin-6, tumor necrosis factor, platelet activating factor, and many of the vasoactive fatty acids derived from arachidonic acid metabolism have been implicated (17). The contribution of oxygen-free radicals, endo-toxin, prostaglandins and thromboxanes in promoting tissue destruction has been supported by the evidence that inhibition of bacterial translocation and mucosal injury has been achieved using allopurinol (27) (an inhibitor of xanthine oxidase), endotoxin desensitiza-tion (28), prostaglandin analogs (29) and thromboxane synthetase inhibitors (30).

The evidence implicating the role of neutrophils in adult respiratory distress syndrome (ARDS) is substantial but indirect (31). Some of the first suggestions that neutrophils may cause an ARDS-like picture were found in severely neutropenic patients who were infused intravenously with donor neutrophils. Occasionally, within hours of neutrophil infusion, there was an abrupt "white-out" of the lungs (by x-ray) and onset of ARDS symptoms. Numerous studies have shown that neutrophils accumulate in the lung during ARDS. For example, their presence has been demonstrated histologically. During the early phases of ARDS, the number of circulating whole blood cells transiently decreases, probably due to their abnormal pulmonary sequestration. Some neutrophils that accumulate within lung capillaries leave the vascular space and migrate into the interstitium and alveolar airspaces. In normal healthy volunteers, neutrophils account for less than 3% of the cells that can be obtained by bronchoalveolar lavage (BAL). In patients with ARDS, the percentage of neutrophils in the lavage is markedly increased to 76–85%. The accumulation of neutrophils is associated with evidence of their activation. They demonstrate enhanced chemotaxis and generate abnormally high levels of oxygen metabolites following in vitro stimulation. Elevated concentrations of neutrophil secretory products, such as lactoferrin, have been detected in the plasma of patients with ARDS. Further evidence that neutrophils actively participate in lung injury was obtained from a clinical study of patients with mild lung injury who were neutropenic for an unrelated reason (e.g., receiving chemotherapy). It was noted that lung impairment frequently worsened if a patient's hematological condition improved and circulating neutrophil counts recovered to normal levels.

Although the evidence implicating neutrophils in the genesis of human ARDS is still largely indirect, data demonstrating the importance of neutrophils in various animal models of acute lung injury is convincing. The common approach that has been used to demonstrate neutrophil independence is to deplete the animal of circulating neutrophils and measure any diminution in lung injury that occurs. Although a number of experimental models have been used to study neutrophil dependence of lung injury, only a few have been selected for discussion herein because of space limitations.

One extensively studied model is the administration of endotoxin to sheep. When endotoxin is intravenously infused into sheep, a complex set of events occurs, one of which is increased permeability of the pulmonary capillary endothelium. This is manifested by an increase in the flow of lung lymph which contains a higher-than-normal protein concentration. These changes indicate a reduction in the ability of the capillary endothelium to retain plasma proteins within the vascular space. The neutrophil dependence of the permeability injury was established when it was found that neutrophil depletion of the sheep prior to endotoxin infusion protected them. Another in vitro model of acute lung injury involves the intravenous infusion of cobra venom factor into rats, which causes complement activation followed by leukoaggregation and sequestration of neutrophils within the pulmonary microvasculature. Alveolar wall damage occurs, leading to interstitial and intra-alveolar edema with hemorrhage and fibrin deposition. Again, neutrophil depletion prevented the increased pulmonary capillary leak.

Isolated, perfused rabbit or rat lungs have also been used to study mechanisms of alveolar injury under circumstances that allow improved control of the variables that affect fluid flux. When neutrophils were added to the perfusate and then stimulated, albumin leaked from the vascular compartment into the lung interstitium and alveolar airspaces. Unstimulated neutrophils or stimulus alone (e.g., phorbol myristate acetate) failed to increase alveolar-capillary permeability.

As further proof that stimulated neutrophils can independently injure lung tissue, in vitro experiments have been performed using vascular endothelial and lung epithelial cells as targets. In some reports, neutrophils have been shown to detach endothelial cells or alveolar epithelial cells from the surface of the tissue culture dish. Obviously, if such an event were to occur in vivo, the denuded surfaces would permit substantial leakage of plasma contents. Furthermore, many reports have provided clear evidence that stimulated neutrophils are able to facilitate lysis of cultured vascular endothelial cells and alveolar epithelial cells.

DHEA is an endogenous androgenic steroid which has been shown to have a myriad of biological activities. Araneo et al (32) has shown that the administration of DHEA to burned mice within one hour after injury resulted in the preservation of normal immunologic competence, including the normal capacity to produce T-cell-derived lymphokines, the generation of cellular immune responses and the ability to resist an induced infection. Eich et al (33, 34) describes the use of DHEA to reduce the rate of platelet aggregation and the use of DHEA or DHEA-sulfate (DHEA-S) to reduce the production of thromboxane, respectively.

Nestler et al. (35) shows that administration of DHEA was able in human patients to reduce body fat mass, increase muscle mass, lower LDL cholesterol levels without affecting HDL cholesterol levels, lower serum apolipoprotein B levels, and not affect tissue sensitivity to insulin. Kent (36) reported DHEA to be a "miracle drug" which may prevent obesity, aging, diabetes millitus and heart disease. DHEA was widely prescribed as a drug treatment for many years. However, the Food and Drug Administration recently restricted its use. DHEA is readily interconvertible with its sulfate ester DHEA-S through the action of intracellular sulfatases and sulfotransferases.

Despite the above discoveries concerning effects of various compounds on burns, there is a need to identify additional compounds which are able to prevent or reduce reperfusion injury as a consequence of ischemia, effects of ischemia associated with infarctions or traumatic injury, and to identify compounds which are able to prevent or reduce bacterial translocation and ARDS. Thus, it is an object of the present invention to prevent or reduce progressive tissue necrosis, to prevent or reduce reperfusion injury, to prevent or reduce bacterial translocation, and to prevent or reduce ARDS.

SUMMARY OF THE INVENTION

The present invention is directed to a method for preventing or reducing reducing reperfusion injury following ischemia, cellular damage associated with ischemic episodes, such as infarction or traumatic injury, and thus to prevent or reduce the consequent progressive necrosis of tissue associated with such ischemia. The present invention is also directed to a method for preventing or reducing bacterial translocation. The present invention is further directed to a method for preventing or reducint ARDS. Finally, the present invention is directed to a method for inhibiting the expression of p-selectin on endothelium. Reperfusion injury is prevented or reduced by administering DHEA, DHEA derivatives or DHEA congeners (collectively referred to as DHEA congeners) to a patient following, e.g., an infarction or traumatic injury. Similarly, bacterial translocation is prevented or reduced in a patient by administering DHEA congeners. ARDS is also prevented or reduced in a patient by administering DHEA congeners. Similarly, p-selectin expression by the endothelium is prevented or reduced in a patient by administering DHEA congeners.

DETAILED DESCRIPTION OF THE INVENTION

Figure 1:
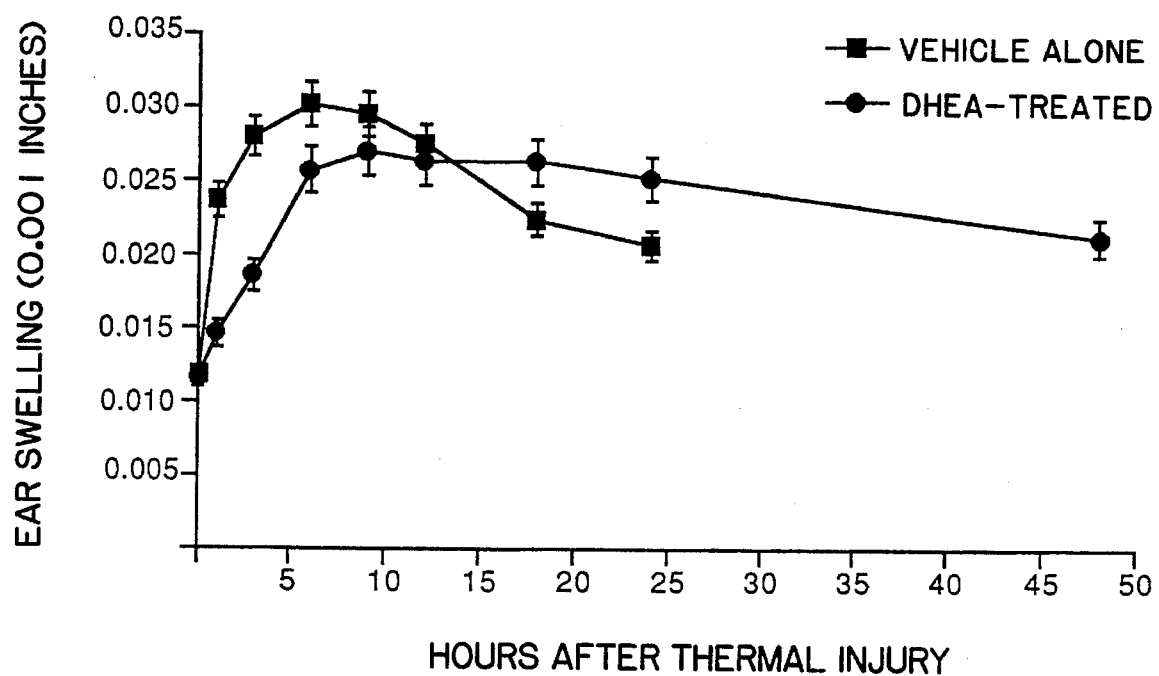
FIG. 1 shows the results of the analysis of edema formation (ear swelling) and resolution in the burned ears of control and DHEA-treated mice.

The present invention is directed to a method for preventing or reducing reperfusion injury following ischemia, and cellular damage associated with ischemic episodes, such as infarction or traumatic injury. An example of an infarction is a myocardial infarction. Examples of traumatic injury include thermal injury, surgery, chemical burns, blunt trauma or lacerations and the like. By preventing or reducing reperfusion injury following ischemia and cellular damage associated with ischemic episodes, the consequent progressive necrosis of tissue associated with such infarction or injury is also prevented or reduced. In accordance with the present invention, reperfusion injury or cellular damage associated with ischemic episodes, such as infarction or traumatic injury, is prevented or reduced by administering DHEA, DHEA derivatives or DHEA congeners to a patient as early as possible, preferably within four hours, and most preferably within two hours, of the ischemia, infarction or traumatic injury.

The present invention is also directed to a method for preventing or reducing bacterial translocation. In accordance with the present invention, bacterial translocation is prevented or reduced in a patient by administering DHEA, DHEA derivatives or DHEA congeners as described above. The DHEA congeners is administered within 24 hours of an injury in which bacterial translocation is one of the sequelae.

The present invention is also directed to a method for preventing or reducing adult respiratory distress syndrome (ARDS). In accordance with the present invention, ARDS is prevented or reduced in a patient by administering DHEA, DHEA derivatives or DHEA congeners as described above. The DHEA congeners is administered prior to clinical symptoms of ARDS, primarily to individuals at risk for ARDS.

Examples of "DHEA", "DHEA congener" or "DHEA-derivative", include but are not limited to, compounds having the formula

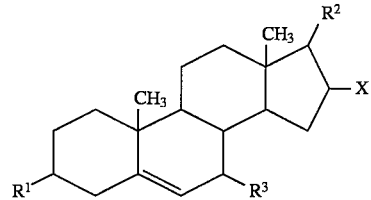

wherein

X is H or halogen;

$R^1$, $R^2$ and $R^3$ are independently =O, —OH, —SH, H, halogen, pharmaceutically acceptable ester, pharmaceutically acceptable thioester, pharmaceutically acceptable ether, pharmaceutically accceptable thioether, pharmaceutically acceptable inorganic esters, pharmaceutically acceptable monosaccharide, disaccharide or oligosaccharide, spirooxirane, spirothirane, —$OSO_2R^5$ or —$OPOR^5R^6$;

$R^5$ and $R^6$ are independently —OH, pharmaceutically acceptable esters or pharmaceutically acceptable ethers; and pharmaceutically acceptable salts.

Thus, examples of suitable DHEA congeners include compounds in which:

(1) $R^2$ is =O, $R^3$ and X are each H and $R^1$ is =O, —OH, pharmaceutically acceptable esters thereof, pharmaceutically acceptable ethers thereof or pharmaceutically acceptable salts;

(2) $R^2$ is =O, $R^3$ is H, X is halogen and $R^1$ is =O, —OH, pharmaceutically acceptable esters thereof, pharmaceutically acceptable ethers thereof or pharmaceutically acceptable salts;

(3) $R^2$ is =O, $R^3$ and X are each H and $R'$ is —SH, pharmaceutically acceptable thioesters thereof, pharmaceutically acceptable thioethers thereof or pharmaceutically acceptable salts;

(4) $R^2$ is =O, $R^3$ is H, X is halogen and $R^1$ is —SH, pharmaceutically acceptable thioesters thereof, pharmaceutically acceptable thioethers thereof or pharmaceutically acceptable salts;

(5) $R^2$ is =O, X is H and $R^1$ and $R^3$ are independently =O, —OH, pharmaceutically acceptable esters thereof, pharmaceutically acceptable ethers thereof or pharmaceutically acceptable salts;

(6) $R^2$ is =O, X is halogen and $R^1$ and $R^3$ are independently =O, —OH, pharmaceutically acceptable esters thereof, pharmaceutically acceptable ethers thereof or pharmaceutically acceptable salts;

(7) $R$: is =O, X is H and $R^1$ and $R^3$ are independently —SH, pharmaceutically acceptable thioesters thereof, pharmaceutically acceptable thioethers thereof or pharmaceutically acceptable salts;

(8) $R^2$ is =O, X is halogen and $R^1$ and $R^3$ are independently —SH, pharmaceutically acceptable thioesters thereof, pharmaceutically acceptable thioethers thereof or pharmaceutically acceptable salts;

(9) $R^2$ is —OH, $R^3$ and X are each H and $R^1$ is =O, —OH, pharmaceutically acceptable esters thereof, pharmaceutically acceptable ethers thereof or pharmaceutically acceptable salts;

(10) $R^2$ is —OH, $R^3$ is H, X is halogen and $R^1$ is =O, —OH, pharmaceutically acceptable esters thereof, pharmaceutically acceptable ethers thereof or pharmaceutically acceptable salts;

(11) $R^2$ is —OH, $R^3$ and X are each H and $R^1$ is —SH, pharmaceutically acceptable thioesters thereof, pharmaceutically acceptable thioethers thereof or pharmaceutically acceptable salts;

(12) $R^2$ is —OH, $R^3$ is H, X is halogen and $R^1$ is —SH, pharmaceutically acceptable thioesters thereof, pharmaceutically acceptable thioethers thereof or pharmaceutically acceptable salts;

(13) $R^2$ is —OH, X is H and $R^1$ and $R^3$ are independently =O, —OH, pharmaceutically acceptable esters thereof, pharmaceutically acceptable ethers thereof or pharmaceutically acceptable salts;

(14) $R^2$ is —OH, X is halogen and $R^1$ and $R^3$ are independently =O, —OH, pharmaceutically acceptable esters thereof, pharmaceutically acceptable ethers thereof or pharmaceutically acceptable salts;

(15) $R^2$ is —OH, X is H and $R^1$ and $R^3$ are independently —SH, pharmaceutically acceptable thioesters thereof, pharmaceutically acceptable thioethers thereof or pharmaceutically acceptable salts;

(16) $R^2$ is —OH, X is halogen and $R^1$ and $R^3$ are independently —SH, pharmaceutically acceptable thioesters thereof, pharmaceutically acceptable thioethers thereof or pharmaceutically acceptable salts;

(17) $R^2$ is —SH, $R^3$ and X are each H and $R^1$ is =O, —OH, pharmaceutically acceptable esters thereof, pharmaceutically acceptable ethers thereof or pharmaceutically acceptable salts;

(18) $R^2$ is —SH, $R^3$ is H, X is halogen and $R^1$ is =O, —OH, pharmaceutically acceptable esters thereof, pharmaceutically acceptable ethers thereof or pharmaceutically acceptable salts;

(19) $R^2$ is —SH, $R^3$ and X are each H and $R^1$ is —SH, pharmaceutically acceptable thioesters thereof, pharmaceutically acceptable thioethers thereof or pharmaceutically acceptable salts;

(20) $R^2$ is —SH, $R^3$ is H, X is halogen and $R^1$ is —SH, pharmaceutically acceptable thioesters thereof, pharmaceutically acceptable thioethers thereof or pharmaceutically acceptable salts;

(21) $R^2$ is —SH, X is H and $R^1$ and $R^3$ are independently =O, —OH, pharmaceutically acceptable esters thereof, pharmaceutically acceptable ethers thereof or pharmaceutically acceptable salts;

(22) $R^2$ is —SH, X is halogen and $R^1$ and $R^3$ are independently =O, —OH, pharmaceutically acceptable esters thereof, pharmaceutically acceptable ethers thereof or pharmaceutically acceptable salts;

(23) $R^2$ is —SH, X is H and $R^1$ and $R^3$ are independently —SH, pharmaceutically acceptable thioesters thereof, pharmaceutically acceptable thioethers thereof or pharmaceutically acceptable salts;

(24) $R^2$ is —SH, X is halogen and $R^1$ and $R^3$ are independently —SH, pharmaceutically acceptable thioesters thereof, pharmaceutically acceptable thioethers thereof or pharmaceutically acceptable salts;

(25) X is H and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(26) X is halogen and $R^1$, $R^2$ and $R^3$ are independently =O, —OH, a sugar residue, pharmaceutically acceptable esters thereof, pharmaceutically acceptable ethers thereof or pharmaceutically acceptable salts, wherein at least one of $R^1$, $R^2$ and $R^3$ is a sugar residue;

(27) X is H and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester;

(28) X is halogen and $R^1$, $R^2$ and $R^3$ are independently =O, —OH, pharmaceutically acceptable inorganic esters thereof or pharmaceutically acceptable salts, wherein at least one of $R^1$, $R^2$ and $R^3$ is an inorganic ester.

Pharmaceutically acceptable esters or thioesters include, but are not limited to, esters or thioesters of the formula —OOCR or —SOCR, wherein R is a pharmaceutically acceptable alkyl, alkenyl, aryl, alkylaryl, arylalkyl, spingosine or substituted spingolipid groups, such as propionate, enanthate, cypionate, succinate, decanoate and phenylpropionate esters.

Pharmaceutically acceptable ethers or thioethers include, but are not limited to, ethers or thioethers of the formula —OR or —SR, wherein R is as defined above or enol, or —$OR^4$ is an unsubstituted or substituted spirooxirane or —SR is a spirothiane.

Suitable sugar residues include, but are not limited to monosaccharides, disaccharides and oligosaccharides, such as a glucuronate.

Pharmaceutically acceptable inorganic esters include, but are not limited to, inorganic esters of the formula —$OSO_2R^5$ or —$OPOR^5R^6$, wherein $R^5$ and $R^6$ are independently —OH, pharmaceutically acceptable esters, pharmaceutically acceptable ethers or pharmaceutically acceptable salts.

Other suitable DHEA congeners can be readily identified by administering the DHEA congener in the burn model described herein and noting its anti-progressive ischemic effect.

It is known that reperfusion injury, infarctions and traumatic injury, such as myocardial infarctions, burns, major surgery, chemical burns, blunt trauma, lacerations and the like, can lead injury in which tissue necrosis extends beyond the directly affected tissue to include surrounding unaffected tissue. This ischemia plays an important role in defining the ultimate tissue pathology observed as a consequence of traumatic injury in humans (10). It is also known that one consequence of thermal injury is bacterial translo-cation. Thermal injury, i.e., burns, is the best studied traumatic injury in which progressive ischemia occurs.

The loss of viable skin through the process of progressive ischemic necrosis contributes significantly to much of the skin loss that requires surgical grafting following burn injury (37). A number of animal models have been developed which mimic very closely many aspects of clinical burns. For example, following the administration of an experimental full-thickness scald burn which covers >20% of the total body surface area to rodents (e.g., 72° C. hot water exposure for 7 seconds), the immediate tissue effects of the burn injury appear quite moderate, compared to the extensive damage to the affected and surrounding skin tissue which develops over the subsequent 24–72 hour period. Thus, it has been observed in both clinical and experimental burns that the total amount of skin lost to a severe thermal injury represents the sum of the immediate direct tissue destruction plus the latent damage that occurs to the epidermis, dermis and inclusive skin structures of the affected and surrounding skin areas.

Initial investigations using the dorsal skin thermal injury model in rodents led to some dramatic findings. It was discovered that scald burn-injured mice that are treated within one hour after thermal injury with the weakly androgenic steroid hormone, dehydroepiandrosterone (DHEA), develop and resolve their wounds in a manner quite distinct from untreated or sham treated thermally injured controls. By 3–4 days after thermal injury, all control-injured animals demonstrate third and fourth degree damage to the vast majority of skin tissue within the injury site. Virtually all of the skin within the affected area is ultimately lost as a consequence of progressive ischemic necrosis. The extent of tissue damage in these animals associates with a major loss in skin structures (hair follicles, blood vessels, neurons, and sebaceous glands), an infiltration of fibroblasts, extensive wound contraction, and the formation of numerous fibrous adhesions under the affected skin area. The DHEA-treated animals (about 2 mg/kg/day after an initial loading dose of 4 mg/kg), however, are observed to develop significantly less pathology, with much less evidence of progressive damage to the dermis, subdermis and associated skin structures. While re-epithelialization is active in both the burn control and the DHEA-treated injured groups of mice, DHEA-treated mice demonstrate much less wound contraction with notably less formation of fibrous adhesions underlying the wound site.

With the use of the dorsal skin injury model, it was clearly demonstrated that DHEA treatment exerts a very positive influence on wound progression. These findings suggested that treatment of thermally injured animals with DHEA may influence wound healing based on a fundamental capacity to prevent ischemia. Consequently, a modification of the procedure first described by Boykin et al., (13) and Eriksson et al., (38) was developed to permit a kinetic evaluation and quantification of progressive dermal ischemia during the immediate and later phases of thermally-injured mouse ears. The technique employed in these studies facilitated a rigorous and sequential monitoring of the time-dependent progression of tissue damage and ischemic necrosis in mouse ears subjected to a hot water scald burn (52° C. for 24 seconds), and has become a valid animal model for investigating progressive ischemia of burn-injured tissue.

The mouse ear consists of two layers of skin, cartilage, sparse muscle cells and connective tissue. Organization of the ear vasculature is well-ordered, comprised of arterioles, precapillary arterioles, post-capillary venules and venules. Employing an apparatus capable of administering controlled thermal injury to the entire surface area of the mouse ear, researchers have reported observing an immediate change in blood flow patterns. As a result of precise morpho-logical studies on hemodynamic changes following burn injury of the mouse ear, three distinct zones, easily separable by the degree of pathology, have been described. These zones comprise the zone of complete capillary occlusion, the zone of partial occlusion (stasis), and the zone of capillary hyperemia (13). By one hour after injury, the area of total capillary occlusion is restricted to the distal margin of the mouse ear. Located more proximally to this outermost, and immediately sensitive area, is the zone of partial occlusion or stasis. It is this major area of ear tissue which becomes progressively ischemic over the 24–72 hour period following thermal injury, and which ultimately undergoes necrosis. Finally, the most proximal area of the affected ear is the zone of hyperemia. This area is fairly resistant to progressive post-burn ischemia.

It has been discovered that the administration to a patient of a therapeutically effective amount of a DHEA congener in a physiologically acceptable carrier as early as possible, preferably within four hours of a reperfusion injury, infarction or traumatic injury, results in the prevention or the reduction of reperfusion injury, infarction or traumatic injury-associated ischemia. The prevention or reduction of the ischemia results in prevention or reduction of the consequent necrosis of tissue associated with such ischemia. This reduction in ischemia results from the reduction of adherence of neutrophils to endothelial cells, as shown in the Example. As a consequence of the reduced neutrophil adherence, the neutrophils do not become activated and do not produce cellular factors which lead to platelet aggregation. It is most preferred that the DHEA congner be administered within two hours of the patient's sustaining the reperfusion, infarction or traumatic injury. The DHEA congener is administered to patients in ester or other pharmaceutically acceptable form and within binders, elixirs or other pharmaceutically acceptable mixtures, or with other pharmaceutically acceptable carriers. It is preferred that the DHEA congener be administered by intravenous injection Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

The dose of the DHEA congener should be based on well known pharmaceutically acceptable principles, e.g., 1–200 mg/kg, preferably 2–50 mg/kg, of the active ingredient. The dose may be administered daily or every other day, and may be taken as single or multiple doses to give the proper daily dosage. For unprotected compounds, i.e., those which can be sulfated by human sulfotransferases or sulfatases, it is preferred to administer an excess dose to insure that sufficient active agent is administered, especially if sulfatases are not active at the site of tissue injury. It has now been discovered that DHEA-S, if administered in a sufficiently high dose such that it is converted to the dosage of DHEA, can be used to prevent progressive ischemia. It is preferred that unprotected compounds be administered daily, whereas protected compounds can be administered either daily or every other day. It is preferred to administer the DHEA congener intravenously. The dosage of DHEA congener utilized will deliver an equivalent of 10–100 mg/kg of DHEA. The dose of DHEA-S necessary to deliver this level of DHEA is 10–1,000 mg/kg, preferably 50–800 mg/kg. The patient is treated with the DHEA congener for 3–30 days, preferably 7–14 days, following the infarction or traumatic injury.

For those patients who are at high risk for a mycocardial infarction or at risk for reperfusion injury, it is possible to prevent or reduce progressive ischemia associated with such an infarction or reperfusion injury by administering the DHEA congener prior to, simultaneously and/or following the infarction or reperfusion injury in the dosages described above. The treatment following the myocardial infarction is as described above. The DHEA congener can be administered to such a patient who demonstrates the classical signs for an imminent myocardial infarction in the same manner as described above for treatment following such an infarction.

For those patients who are at risk of bacterial translocation, such bacterial translocation is prevented or reduced by administering the DHEA congener as described above in the dosages described above. The administration to prevent or reduce bacterial translocation continues until the patient is no longer at risk for the bacterial translocation.

It has been discovered that it is critical that the DHEA congener be administered soon after reperfusion injury, infarction or traumatic injury in order to prevent or reduce any cellular damage. If the administration of these compounds occurs too late, blood vessels will become occluded (initially with neutrophils adhering to endothelial cells), at which point the administration of these compounds will be unable to prevent or reduce the ischemia. The time frame within which the administration should begin may be dependent on the type of reperfusion injury, infarction or traumatic injury, and can be readily determined by appropriate animal models. However, it is preferred that administration of the DHEA congener commence within four hours, and most preferably within two hours of the ischemia, infraction or traumatic injury. The administration of the DHEA congeners to prevent or reduce bacterial translocation should begin within 24 hours of the injury or stress-causing event. It is preferred that administration of these compounds to prevent or reduce bacterial translocation begin within four hours, and most preferably within two hours. The administration of the DHEA congeners to prevent or reduce ARDS should begin before the onset of clinical symptoms. Generally, the compounds will be administered to patients at risk of ARDS.

The present invention is described by reference to the following Examples, which are offered by way of illustration and are not intended to limit the invention in any manner. Standard techniques well known in the art or the techniques specifically described below were utilized.

EXAMPLE 1

Experimental Thermal-Injury Model

An experimental thermal injury model employing mouse ears was developed where temperature and exposure time were established empirically. The conditions represented the minimal burn injury which progressed to total tissue necrosis in the exposed ear of untreated mice by 24–72 hours post-burn. Groups of Balb/c mice, approximately nine weeks old, were given an identifying mark, and then divided into control and treated subgroups. The thickness of the ear to be immersed in hot water was recorded, and then the entire ear of the anesthetized mouse was dipped into 52° C. water for exactly 24 seconds. Each mouse was returned to its cage after an injection of either the propylene glycol vehicle (control) or 100 mg of test agent dissolved in propylene glycol. Ear swelling changes were monitored on individual mice at pre-burn, and at various hours after thermal injury.

EXAMPLE 2

Effect of DHEA in the Thermal-Injury Model

Groups of Balb/c mice, approximately 9 weeks old, were given an identifying mark, and then divided into control and treated subgroups. The thickness of the ear to be immersed in hot water was recorded, and then the entire ear of the anesthetized mouse was dipped into 52° C. water for exactly 24 seconds. Each mouse was returned to its cage after an injection of either the propylene glycol vehicle (control) or 100 mg of DHEA agent dissolved in propylene glycol. Ear swelling changes were monitored on individual mice at pre-burn, and at 1, 3, 6, 9, 12, 18, 24 and 48 hours after thermal injury.

The results of the analysis of edema formation and resolution in the ears of control and DHEA-treated mice are shown in FIG. 1. Ear swelling, as a measure of edema, reached a peak in both DHEA-treated and untreated burned mice by six hours after injury. In the untreated group, the extent of swelling started to decline within 12 hours, and continued to decline rapidly over the subsequent 12 hour periods. Between 24 and 48 hours post-burn, ear measurements had to be discontinued in the untreated group due to the complete loss of ear tissue resulting from the complete micro-vascular occlusion of the original zone of stasis. The kinetic analysis of edema in untreated and DHEA-treated thermally-injured mice showed that the events which take place during the first 24 hours following a burn-induced injury are critical to the viability of the thermally-injured tissue, such that the eventual preservation of viable ear tissue at 48 hours correlates inversely with the rate at which the swelling response recedes between the peak at six hours and the final 48 hour time period.

In addition to the analysis of edema in untreated and DHEA-treated thermally-injured mice, the changes in viability of the ear tissue itself were documented photographically. Injury of the ear tissue in mice given only the vehicle was extensive, with greater than 70% of the ear tissue being necrotic and destroyed within 48 hours. The total affected area appeared to encompass both the zone of complete vascular occlusion and the original zone of stasis. This latter zone became damaged as a secondary consequence of thermal injury, a condition which defines progressive post-burn dermal ischemia. However, DHEA-treated mice showed little injury and the preservation of burned ear tissue was seen in a kinetic fashion. The only area of ear tissue that was markedly affected by, but not lost to the effects of thermal injury corresponded to only the original zone of complete vascular occlusion.

EXAMPLE 3

Effect of Various Compounds in the Thermal Injury Model

Groups of nine-week old thermally injured Balb/c mice were divided into subgroups given either vehicle alone, DHEA, androstenediol, 16a-bromo-DHEA, andros-tenedione or the potent anti-glucocorticoid, RU486. Individual mice received 100 mg of the indicated steroids or the vehicle alone immediately post-burn (day 0), and further 50 mg doses every 24 hours for the duration of the experiment. The ear swelling response of each individually marked mouse was recorded at the pre-burn stage, and at 12, 24 and 48 hours post-burn.

Figure 2:
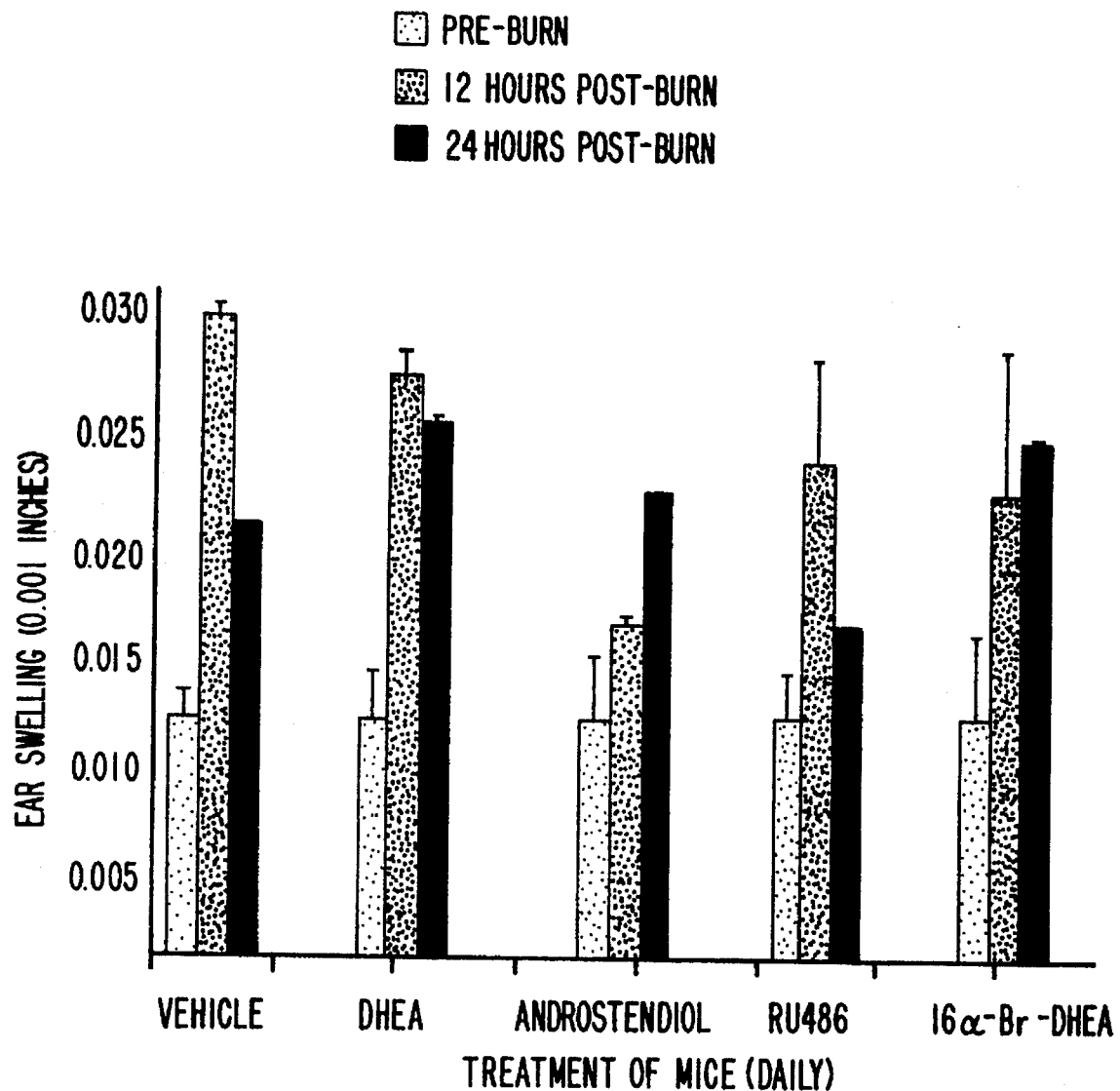
FIG. 2 shows the analysis of edema formation (ear swelling) and resolution in the burned ears of control mice and mice treated with DHEA, androstenediol, 16a-bromo-DHEA or the known anti-glucocorticoid RU486.

Burned ears of mice being treated therapeutically with androstenediol, DHEA, or the non-metabolizable, synthetic derivative of DHEA, 16a-bromo-DHEA, each developed significant ear-swelling in response to burn injury (FIG. 2) and exhibited a slow and constant rate of resolution of the swelling. This slow loss of edema following thermal injury of the ear was paralleled by only minimal dermal ischemia and necrosis in the area. The results of this study also confirmed that the development of edema within the burned ear of untreated mice peaks and then recedes somewhat rapidly, such that between 24–48 hours post-burn a significant amount of tissue ischemia and necrosis takes place. The similar pattern of edema followed by progressive ischemic necrosis was observed with andostenedione-treated mice. Likewise, a similar pattern of edema followed by progressive ischemic necrosis was observed in the group of thermally injured animals treated with RU486, indicating that DHEA is not working solely via its anti-glucocorticoid effects.

Figure 3A:
FIG. 3A shows the capacity of DHEA to protect against most of the progressive ischemia consequences of thermal injury to the ear.
Figure 3B:
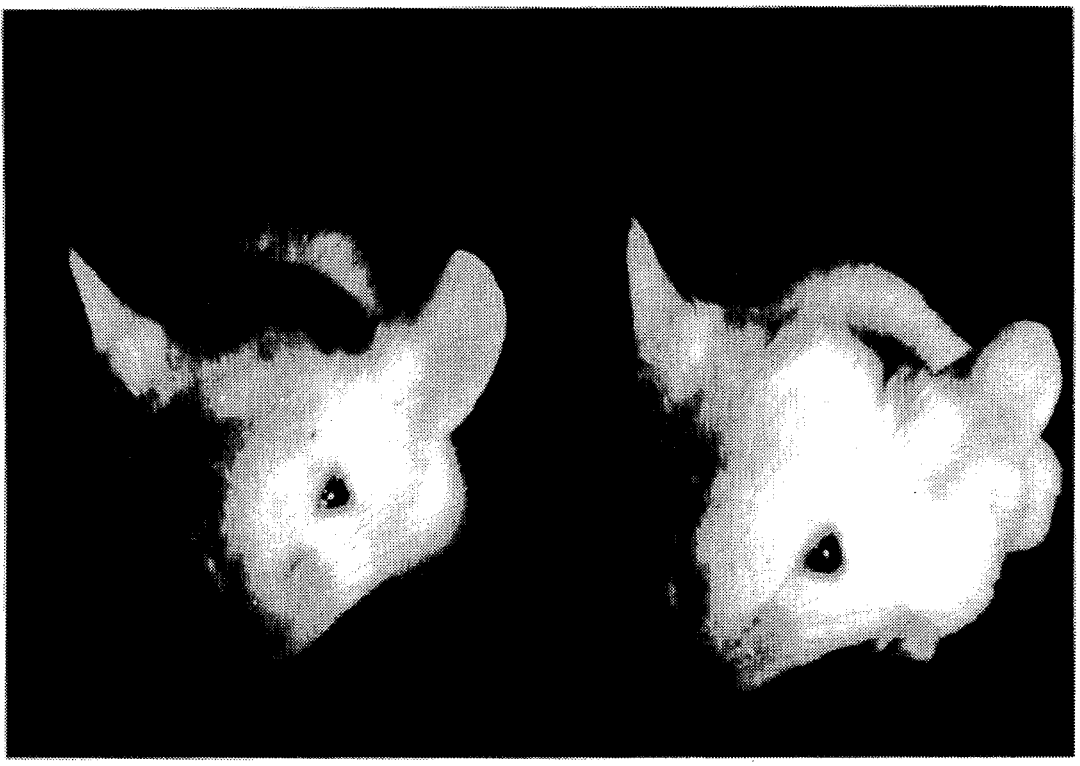
FIG. 3B shows the capacity of androstenediol to protect against most of the progressive ischemia consequences of thermal injury to the ear.
Figure 3C:
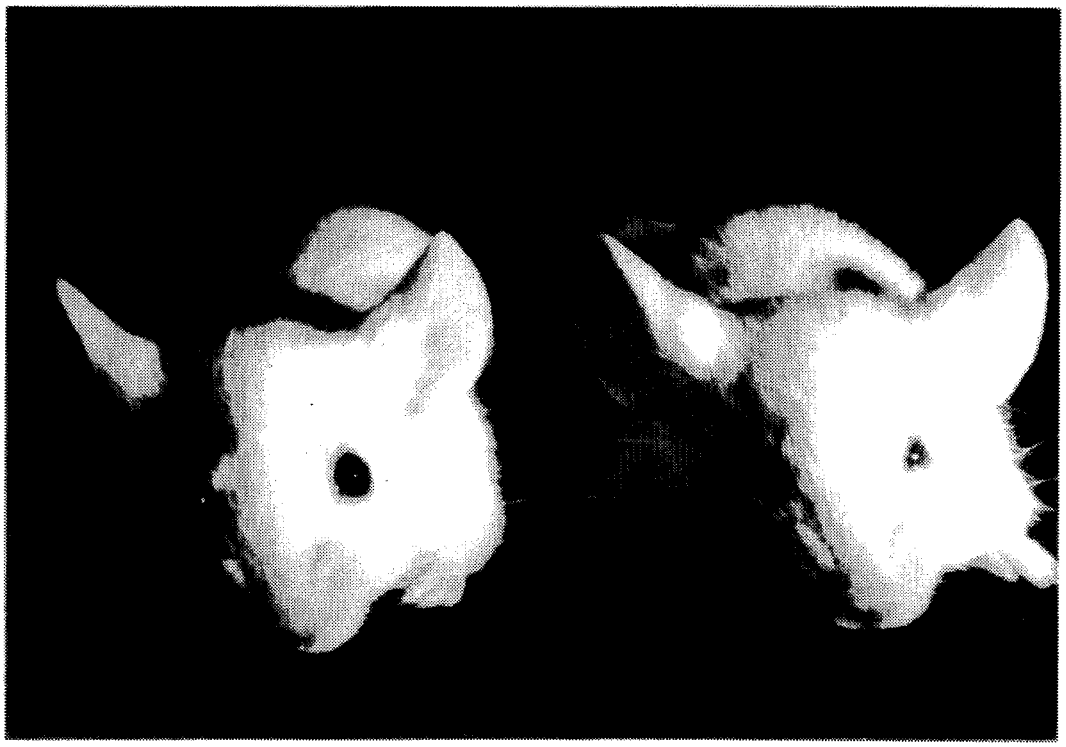
FIG. 3C shows the capacity of 16a-bromo-DHEA to protect against most of the progressive ischemia consequences of thermal injury to the ear.
Figure 3D:
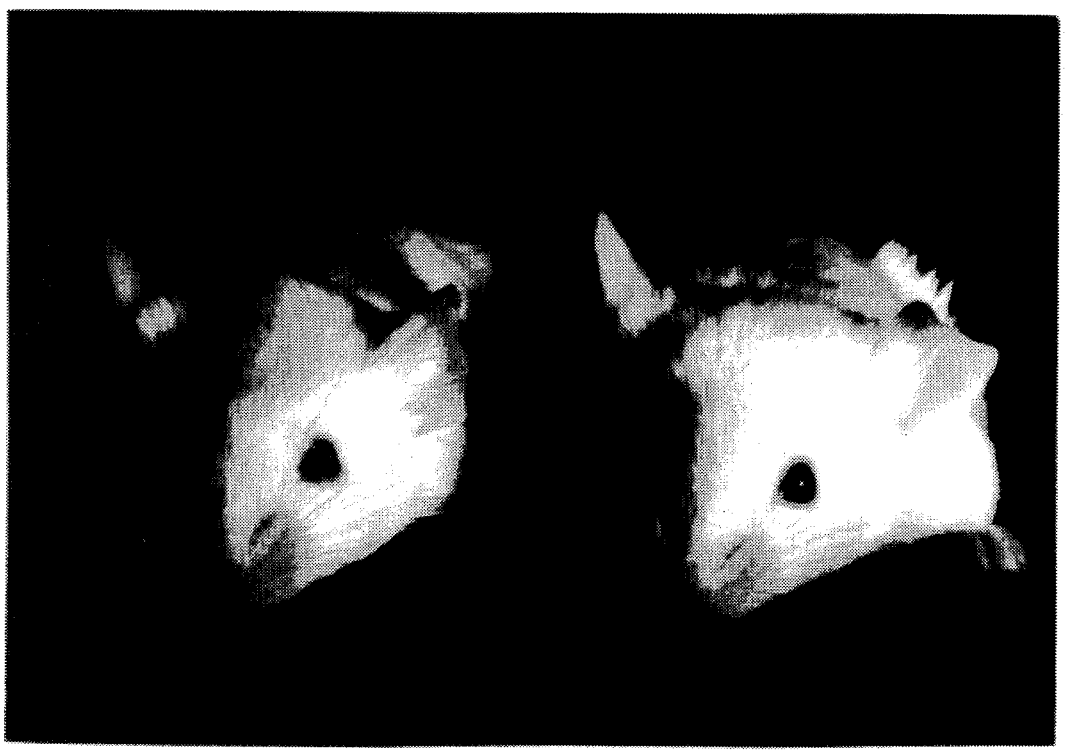
FIG. 3D shows the progressive ischemic consequences of thermal injury to the ear when vehicle alone is administered.
Figure 3E:
FIG. 3E shows the progressive ischemic consequences of thermal injury to the ear when androstenedione alone is administered.
Figure 3F:
FIG. 3F shows the progressive ischemic consequences of thermal injury to the ear when RU486 alone is administered.

FIGS. 3A–3C demonstrate the capacity of DHEA, androstenediol and 16α-bromo-DHEA to protect against most of the ischemic consequences of thermal injury to the ear. Mice treated with either one of these steroid hormones incur early changes in ear tissue with slight to no loss of ear tissue several days after thermal injury. The affected area appears to correspond to the zone of complete occlusion defined by Boykin (13). Mice given the vehicle alone, androstenedione or RU486 (FIGS. 3D–3F) following thermal injury lose >70% of the exposed ear tissue over the first 48 hours post-injury due to progressive post-burn ischemic necrosis. Without effective treatment, the areas of the burn-injured ear which became necrotic corresponded to the zone of complete occlusion plus the zone of stasis. Thus, it was demonstrated that treatment of thermally-injured mice with either DHEA, androstenediol, or 16a-bromo-DHEA not only changes the natural course of the edema produced in the ear but also somehow protects the affected tissue from progressive damage by inhibit-ing the development of ischemia within the zone of stasis and the ultimate development of necrosis of this area.

In similar experiments, it was found that 16α-hydroxy-DHEA was less protective, i.e., reduced the extent of, but did not totally prevent progressive ischemia, and 16α-chloro-DHEA was slightly protective against progressive ischemia.

EXAMPLE 4

Timing of Initial Administration of DHEA

Figure 4:
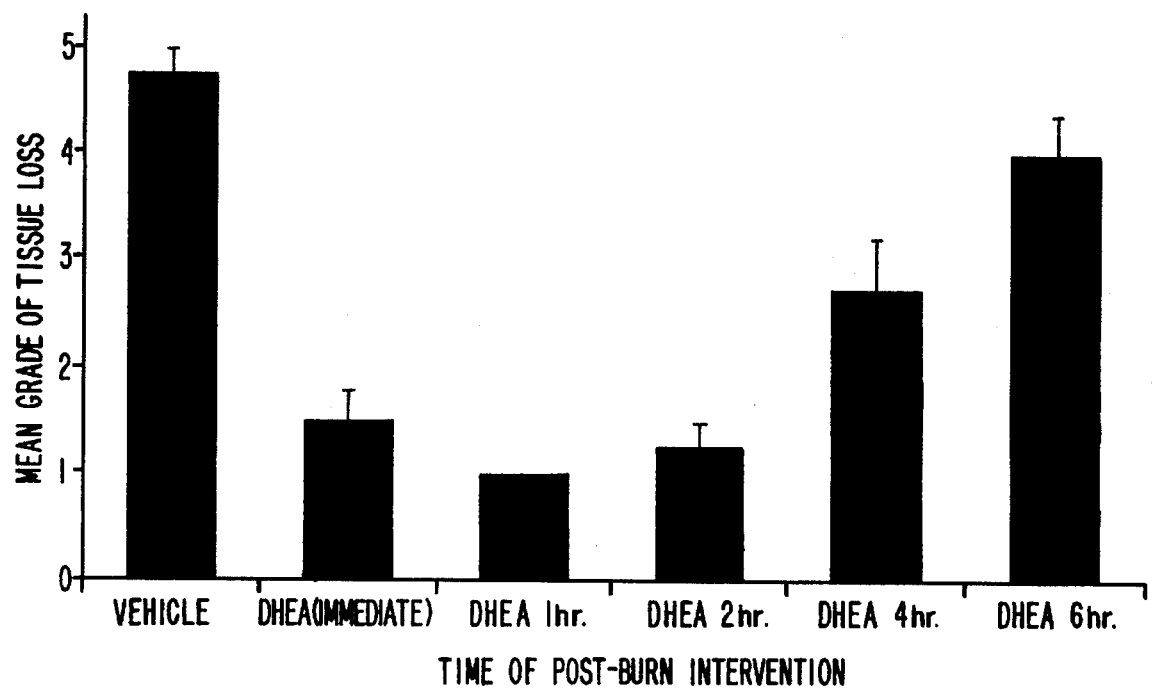
FIG. 4 shows the effect of treatment with DHEA on progressive ischemia when administered from 0–6 hours post-thermal injury.

An experiment was designed to determine whether intervention using DHEA must be delivered immediately, or whether the intervention can be delayed for up to several hours following burn injury. Mice were anesthetized, administered a burn and then, while under anesthesia, four mice were given vehicle alone, four mice were given 100 mg DHEA, and the remaining mice were divided into additional groups of four. All of the mice in a single group would receive 100 mg DHEA either one, two, four or six hours after thermal injury. Tissue loss by each mouse was evaluated 72 hours after thermal injury, and the results of the scoring are presented in FIG. 4.

This Figure demonstrates that intervention using DHEA can be delayed for up to two hours with no significant difference in the protective effects of DHEA mean grade of 1.25% 0.25 ($p=<0.001$). Even with a delay of four hours before administration of DHEA, a mean score of 2.75% 0.479 was observed ($p=<0.016$). With a six-hour delay in delivery of DHEA, the mean score in tissue loss was 4.0% 0.408 and was determined to be significantly different from the group that received DHEA immediately after thermal injury ($p=<0.058$). It was concluded that the events which lead to necrosis are reversible by administration of DHEA for up to several hours post-thermal injury.

The above examples demonstrate that moderate-intensity thermal injury of the mouse ear is a reliable and reproducible model for examining progressive ischemic necrosis of the skin. The results indicate that immediate post-burn use of DHEA has a protective effect on thermal injury-induced dermal ischemia. In addition to DHEA, several other steroid hormones have been tested for their therapeutic value (see Table I).

TABLE 1

| Results of Progressive Steroid Hormone Tested (100 mg/mouse) | Ischemia Analysis (mouse ear model) |
| --- | --- |
| DHEA-S | nonprotective |
| DHEA | protective |
| 16a-Bromo-DHEA | protective |
| androstenediol | protective |
| androstenedione | nonprotective |
| RU 486 | nonprotective |

Along with DHEA, androstenediol and 16a-bromo-DHEA were markedly protective, in that 90–100% of the ear tissue remained intact until the experiment was terminated at two weeks, when the healing process was complete. 16a-Hydroxy-DHEA was less protective and 16a-chloro-DHEA was slightly protective. However, DHEA-sulfate at the dose examined, androstenedione and RU486 were completely nonprotective, in that ear damage and tissue loss equivalent to untreated controls was evident in all animals within 48 hours after thermal injury. It has now been discovered that if a sufficiently high dose of DHEA-S is administered to lead to the equivalent amount of DHEA as used in this experiment, then DHEA-S is protective. The ability to separate protective from nonprotective steroids in this thermal injury model is most likely facilitated by the fact that direct or immediate burn damage to the ear tissue is minimal, and that the vast majority of the damage which occurs emanates from the progressive ischemia and necrosis caused by the host response to the scald-burn.

The results implicate DHEA, not one of its natural metabolites, as the agent mediating protection against progressive ischemic necrosis. The basis for this conclusion is straightforward. 16a-Bromo-DHEA is a DHEA analog which cannot be effectively metabolized to downstream androgen steroids, and its protective effect is identical to DHEA. Androstenediol also displays a biologic effect identical to DHEA in the thermal-injury ear model. This steroid is a natural metabolite of DHEA which, through enzyme-dependent modification, can be converted back to DHEA. It can also be further metabolized to testosterone. Androstenedione, also a secondary metabolite of DHEA, can be metabolized only to downstream products, (e.g., testosterone and estrogens), with no known conversion to DHEA. Because androstenedione cannot protect against progressive dermal ischemia in this model, its lack of effect supports the conclusion that the active steroid is DHEA, not a downstream androgen or estrogen.

DHEA possesses the published ability to overcome some of the biological effects caused by glucocorticoids. The possibility that DHEA functions as an anti-glucocorticoid in the dermal ischemia model of the thermally-injured mouse ear was tested by administering the known anti-glucocorticoid, RU 486, to mice immediately after administration of the burn injury. As presented in this model and under the conditions tested, substances with anti-glucocorticoid activities offered no benefit.

EXAMPLE 5

Effect of DHEA on Reperfusion injury

Male Sprague-Dawley rats weighing 130–170 g were randomly assigned to no pre-treatment, vehicle pre-treatment or DHEA pre-treatment (4 mg/kg). Animals were treated with vehicle or DHEA the day before and the day of surgery. Anesthesia was induced with intraperitoneal pentobarbital (60–70 mg/kg). The rats were placed on a heating pad, and body temperature (measured by rectal probe) was maintained at between 35°–37°C. Detection of the cremaster muscle on its neurovascular pedicle was performed according to conventional techniques (39–41). Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. Finally, the front wall of the cremaster muscle sac is opened and the island cremaster muscle flap is prepared for intravital videomicroscopy. The rat is secured on a specially designed tissue bath, and the cremaster muscle flap is spread over the coverglass in the opening at the bottom of the bath and fixed with 5–0 silk sutures. It is then transilluminated from below, using a fiberoptic tungsten lamp. The muscle is kept moist and covered with impermeable plastic film. The tissue bath, designed specifically for temperature control, is filled with 0.9% saline and the temperature maintained at between 35° C.–36° C. The microscope is equipped with a color video camera. The video image of the microcirculation is displayed on a 19" monitor, where the final magnification is ×1800. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

The following parameters are used to evaluate the state of the cremaster muscle microvasculatory system prior to ischemia and after reperfusion.

Figure 5A:
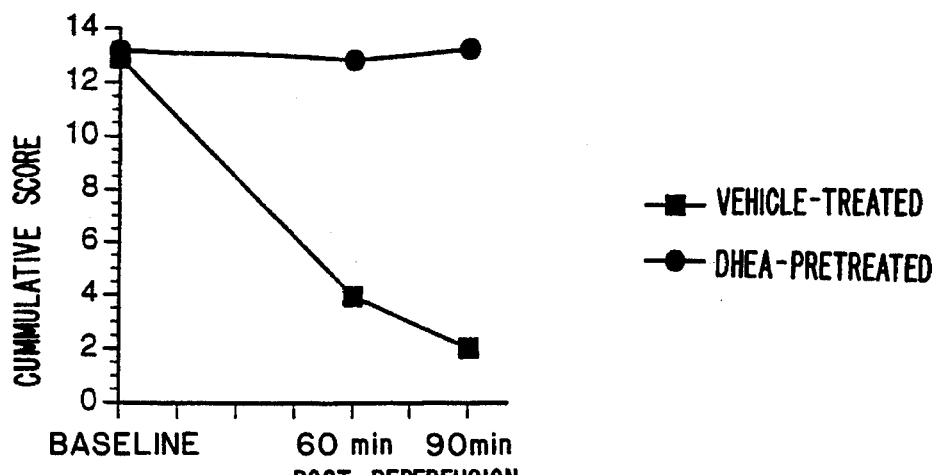
FIG. 5A shows the number of flowing capillaries in proximity to post-capillary venule in Zone 1 during reperfusion injury.
Figure 5B:
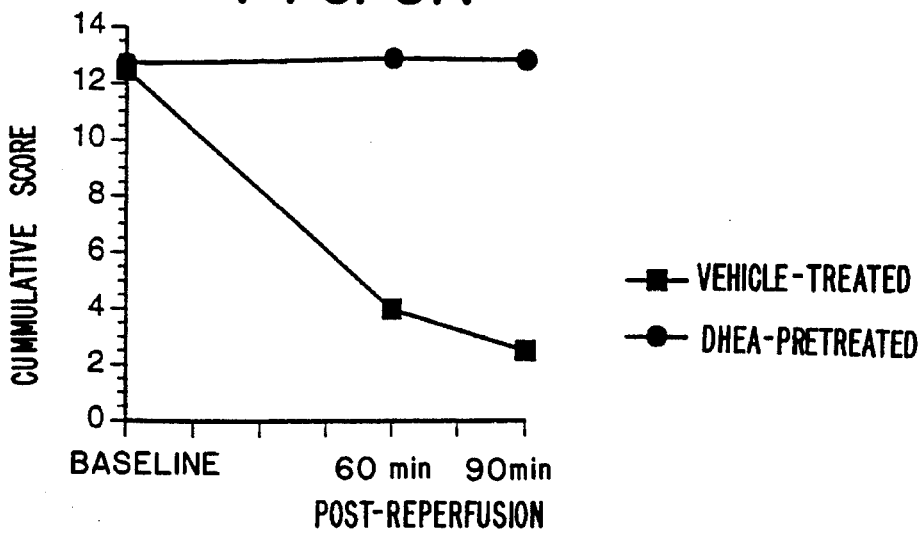
FIG. 5B shows the number of flowing capillaries in proximity to post-capillary venule in Zone 2 during reperfusion injury.
Figure 5C:
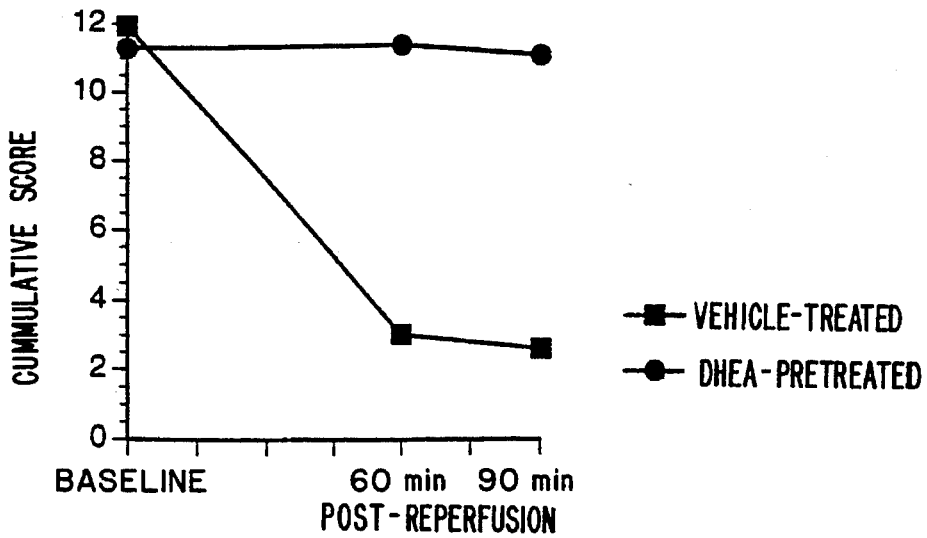
FIG. 5C shows the number of flowing capillaries in proximity to post-capillary venule in Zone 3 during reperfusion injury.

1) Density of Perfused Capillaries. The density of perfused capillaries in each of three flap regions (Zone 1, 2 and 3) is measured by counting the number of flowing capillaries in proximity to the preselected postcapillary venule. Nine visual fields of capillaries are counted at each postcapillary venule site, for a total of 27 fields per cremaster muscle flap. Results are shown in FIGS. 5A, 5B and 5C for Zones 1, 2 and 3, respectively.

Figure 6A:
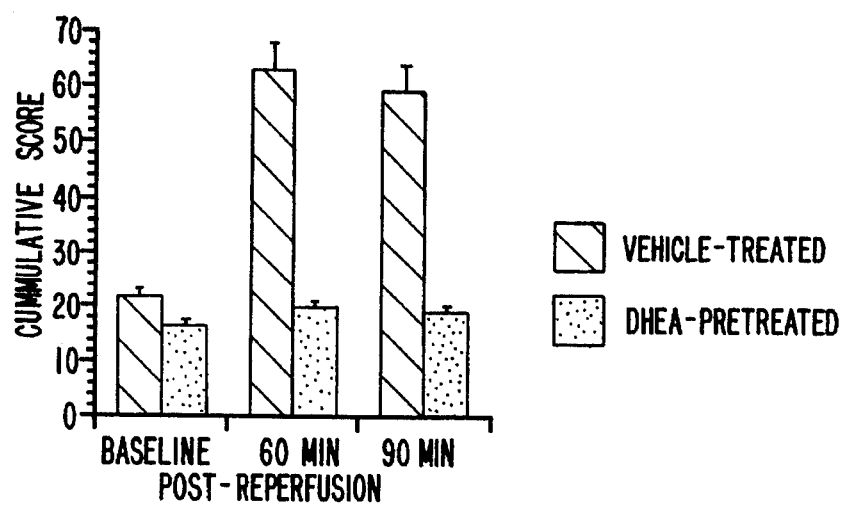
FIG. 6A shows the number of leukocytes rolling through the lumen of post-capillary venules in a two-minute period.
Figure 6B:
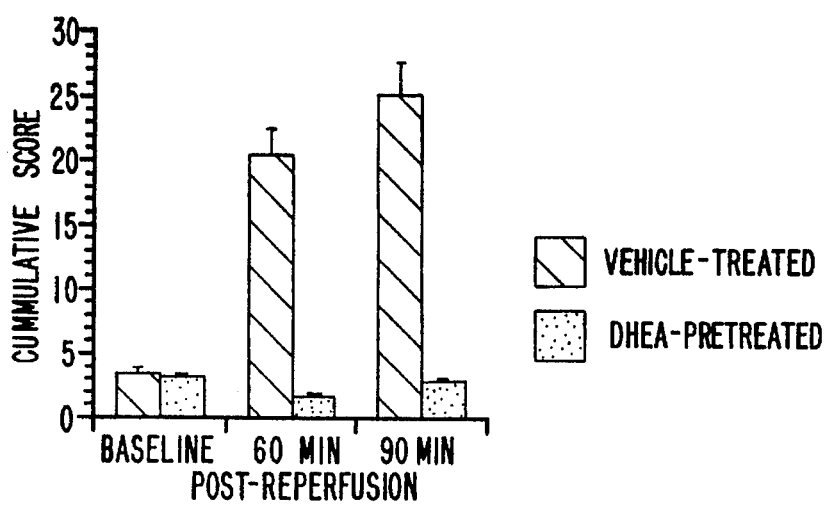
FIG. 6B shows the number of leukocytes adhering or sticking to the lumen of post-capillary venules in a two-minute period.
Figure 6C:
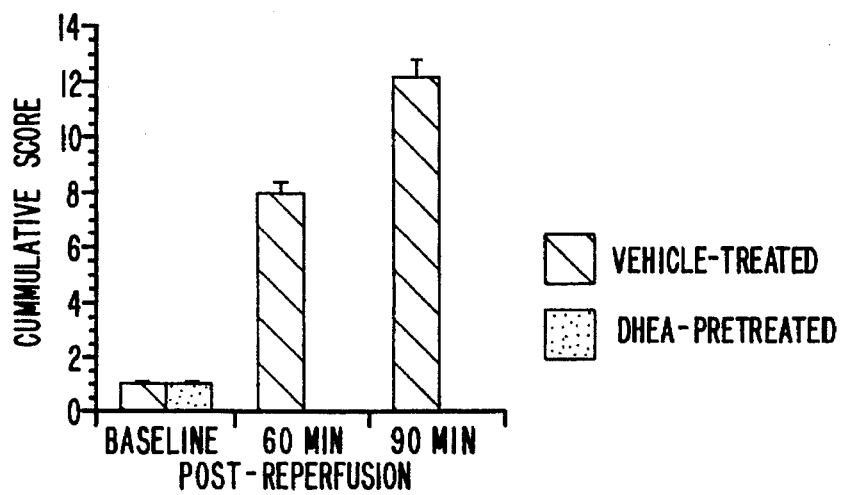
FIG. 6C shows the number of leukocytes migrating across the endothelium in a two-minute period.

2) Leukocyte Count in Postcapillary Venules. Video scans of three pre-selected postcapillary venules are taken in proximal, middle and distal flap regions. For each venule, the number of leukocytes rolling through the luman, the number adhering to the endothelium and the number having migrated across the endothelium over a two-minute period are recorded. Results are shown in FIGS. 6A, 6B and 6C for rollers, strikers and diopedesis, respectively.

Figure 7A:
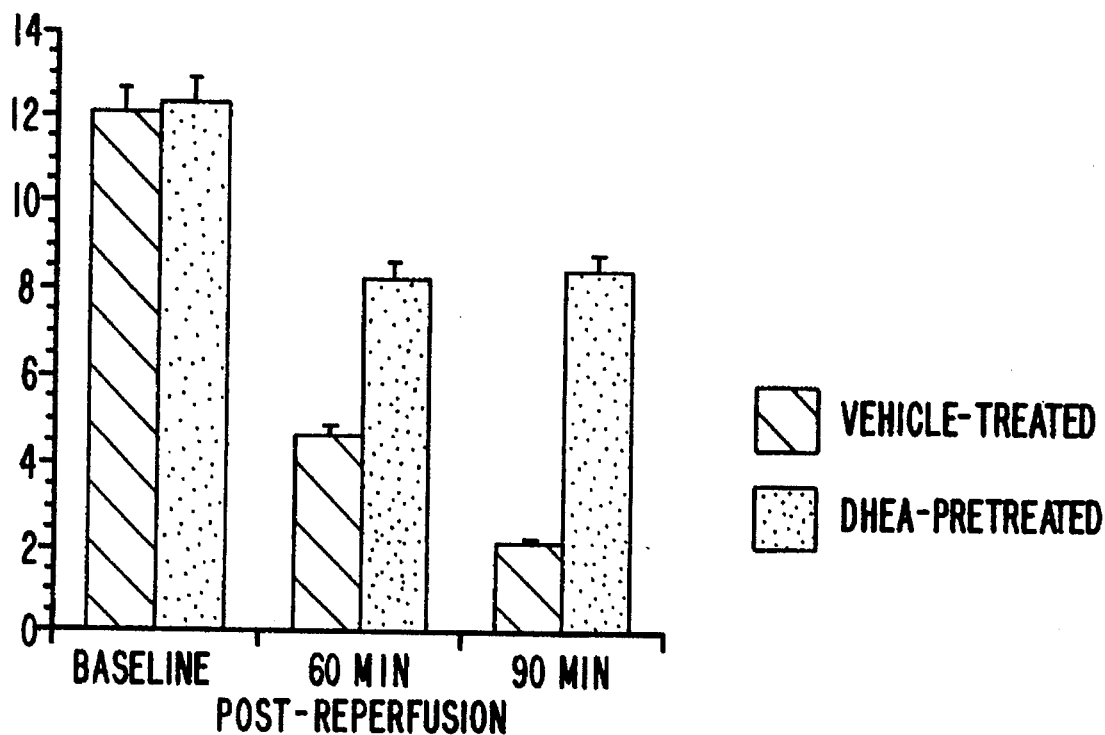
FIG. 7A shows red cell velocity of venous blood post-reperfusion.
Figure 7B:
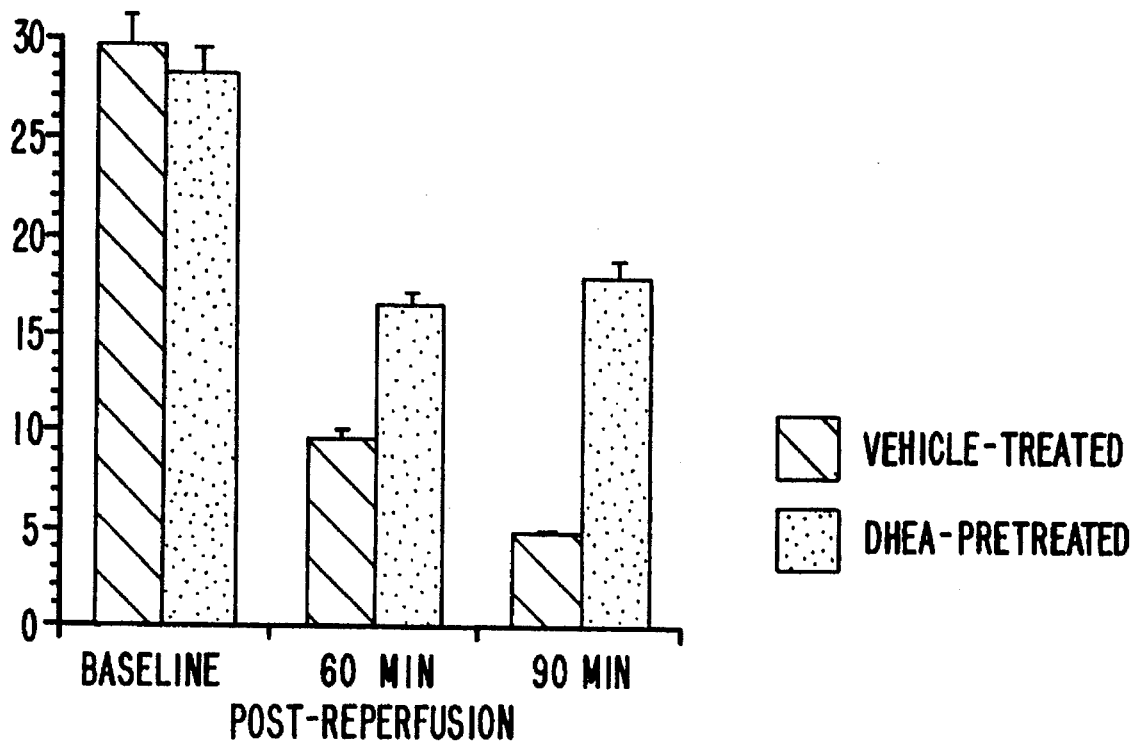
FIG. 7B shows red cell velocity of arterial blood post-reperfusion.

3) Red Blood Cell Velocities in A1 (First Order) and A2 (Second Order) Arterioles. Red blood cell velo-cities are recorded in the main arterioles of the cremaster flap using a custom-made optical Doppler velocimeter. Results are shown in FIGS. 7A and 7B, for velocity of venous and arterial blood, respectively.

A. Reperfusion Injury in Untreated. and Vehicle-Treated Rats

Six rats were untreated and six rats were pre-treated with vehicle. Under conditions of six hours of ischemia and 90 minutes of reperfusion, the absolute number of rolling, sticking and transmigrated leuko-cytes increased dramatically within 60 minutes of reperfusion and showed a further increase at 90 minutes (FIGS. 6A–6C). A dramatic decrease was observed in the absolute number of perfused capillaries per high-powered field that were at both 30 and 60 minutes post-reperfusion, with a continued decrease in numbers of flowing capillaries at 90 minutes post-reperfusion (FIGS. 5A–5C). Likewise, red cell velocities in A2-sized vessels were significantly slower at 60 and 90 minutes post-reperfusion (FIGS. 7A and 7B).

B. Reperfusion Injury in DHEA-Treated Rats

Under conditions where rats were pre-treated with 4 mg/kg DHEA by subcutaneous injection the day before and the day of surgery, a marked and highly significant protective effect of the therapy was measured. All three parameters exhibited values that were close to, or identical with normal values. Of major importance, it was noted that all time-points, endothelial-adherent properties were unchanged from baseline values. This conclusion is based on the fact that numbers of roll-ing, sticking and transmigrating leuko-cytes appeared remarkably similar to baseline values (FIGS. 6A–6C). Red cell velocities in A2 arterioles were slower to return to normal rates of flow, with velocities in some areas measuring 75% of normal at 90 minutes post-reperfusion (FIGS. 7A and 7B). At the 90-minute timepoint, the number of capillaries flowing in the microvasculature were not significantly different from the baseline values obtained prior to ischemia (FIGS. 5A–5C).

Without being bound by any theory of the physiolo-gical and biochemical operation of the DHEA congeners, it is believed that the anti-ischemic effects of these compounds are due to their activity on the adhesion of neutrophils to endothelial cells. Thus, these compounds are effective in preventing or reducing ischemia which may result from other types of tissue injury, which can be modulated by affecting adhesion to endothelial cells. This inhibition of neutrophil adhesion prevents activation of neutrophils and transmigration to the tissue side of the endothelium. Since transmigration of neutrophils is inhibited, neutrophil-in-duced massive damage to endothelial cells and parenchymal cells is prevented. Since neutrophil activation is prevented, production of cellular factors (by neutrophils) which leads to platelet aggregation is also prevented. Thus, progressive tissue necrosis is prevented or reduced. In addition, the progressive ischemia of gut tissue (leading to bacterial translocation) and of the epidermis and of cardiac muscle and the ischemia of the alveolar wall (leading to ARDS) are mediated through similar mechanisms. Thus, these com-pounds are also effective in preventing or reducing bacterial translocation and ARDS.

EXAMPLE 6

Effect of DHEA on Expression of P-Selectin by Platelets

Platelets were fractionated from freshly drawn blood (mature adults and elderly). Platelets were either utilized unwashed or washed. Washed platelets were obtained by conventional procedures (42, 43). Briefly, blood was col-lected to a syringe containing 1 volume of anticoagulant (0.085M sodium citrate, 0.065M citric acid, 2% dextrose) to 7 volumes of blood. Routinely, 50 ml of blood was with-drawn, Blood samples were centrifuged at 180×g from 15 minutes at room temperature to sediment red and white blood cells. The upper two-thirds of the platelet-rich plasma supernatant was carefully removed by aspiration, and the platelets were pelleted by centrifugation at 1100×g for 10 minutes at room temperature. The supernatant was decanted and the platelets were resuspended by gently mixing the sample in 2 ml of washing buffer (Tyrode's buffer without calicium, pH 6.50 at 37° C.). The platelet suspensioin was then diluted to a volume equal to the original volume of blood drawn with Tyrode's buffer, and centrifuged at 1100×g for 10 minutes at room temperature. The platelets were washed twice more by centrifugation and resuspended in 5 ml of incubaiton buffer (washing buffer adujsted to pH 7.4 at 37° C.). The platelets were counted in a Neubauer hemocytometer.

Washed and unwashed platelets were examined for the presence of P-selectin by direct immunostaining. Platelets ($1\times10^6$) were incubated with phycoerythrin-conjugated either negative control antibody or anti-human P-selectin monoclonal antibody (CD62 antibody, CAMFolio, Becton-Dickinson) for 15 minutes on ice. After that time, samples were washed twice with staining buffer (PBS, 0.1% sodium azide, 2% fetal bovine serum), reconstitued in 500 µl of staining buffer and analyzed by a FACScan flow cytometer (Becton Dickinson). The fluorescence was displayed as a single parameter histogram on a linear scale.

Measurement of P-selectin levels on surface of washed platelets obtained from blood of mature individuals showed that approximatley 50% of washed platelets (resting plate-lets) tested positive for the presence of P-selectin. Sixty-eight percent of the unwashed platelets obtained from blood of an elderly individual tested positive for P-selectin. When whole blood form this individual was supplemented with 10 µM final concentration of DHEA prior to fractionation of the platelets and then test, only 12% of the platelets stained positive for P-selectin. This down-regulation of P-selectin by DHEA was accompanied by a 40% reduction in thrombin activated platelet aggregation. When this latter individual was placed on a supplemental therapy with DHEA-S and the platelets fractioned from blood drawn during the supple-mental therapy with DHEA-S, the platelets were refractory to exogenous DHEA when activated with the same amount of thrombin as activated prior to the therapy. Thus, the observed down-regulation of P-selectin on the surface of platelets from elderly individuals by DHEA was accompa-nied by a prevention of thrombin-stimulated aggregation of these platelets by DHEA.

EXAMPLE 7

Effect of DHEA on Expression of P-Selectin by Endothelial Cells

Non-virally transformed Human Dermal Microsvascular Endothelial cells were cultured using conventional tech-niques. Cells in passage number 2 were put on cover slips covered with attachment factor, and were grown in serum free system without phebol red until they became confluent. Groups of cells were incubated with vehicle alone or with 1 µM, 10 µM, 25 µM, 50 µM or 100 µM DHEA at 37° C. for 10 minutes. The cells were then activated with $10^{-5}$M histamine or with Dulbecco's phosphate buffer saline (dPBS) at 37° C. for 5 minutes.

The cells were then examined by indirect immunostain-ing/fluorescence microscopy. Briefly the cells were first washed 2–3 times in dPBS containing 1% bovine serum albumin (BSA), 1–2 minutes per wash. The cells were then fixed in ice-cold methanol for 5–7 minutes and then washed 2–3 times in dPBS containing 1% BSA and 0.01% azide. The cells were then incubated with anti P-selectin antibody at 4° C. in a humified chamber for 30 minutes. The cells were then washed 2–3 times in dPBS containing 1% BSA at 4° C., 1–2 minutes per wash. The cells were then incubated an anti anti-body linked to P-phycoerytherin at 4° C. for 30–40 minutes, after which the cells were washed 2–3 times in dPBS containing 1% BSA at 4° C., 1–2 minutes per wash. The slides are then mounted and and P-selectin expression on endothelium is examined in fluorescence microscopy using rhodamine filterset.

Similary results are noted as seen for P-selectin expres-sion in platelets. Namely, DHEA at concentrations of 10 µM or greater prevented the up-regulation of P-selectin expres-sion normally observed on endothelium in response to histamine. The endothelium incubated with DHEA prior to histamine activation looked similar to the control, non-activated endothelium.

It will be appreciated that the methods and com-positions of the instant invention can be incorporated in the form of a variety of embodiments, only a few of which are disclosed herein. It will be apparent to the artisan that other embodi-ments exist and do not depart from the spirit of the invention. Thus, the described embodiments are illustrative and should not be construed as restrictive.

LIST OF REFERENCES (1) Rodgers, G. M. (1988). *FASEB J* 2:116–123.
(2) Hernandez, L. A. et al. (1987). *Am. J. Physiol.* 253 (Heart Cir. Physiol. 22):H699–H703.
(3) Lucchesi, B. R. (1990). *Am. J. Cardiology* 65:14I–23I.
(4) Lehr, H. A. et al. (199). *J. Clin. Invest.* 87:2036–2041.
(5) Entman, M. L. et al. (1991). *FASEB J* 5:2529–2537.
(6) Weyrich, A. S. et al. (1993). *J. Clin. Invest.* 91:2620–2629.
(7) Lefer, A. M. et al. (1991). *FASEB J* 5:2029–2034.
(8) Brown, J. M. et al. (1988). *J. Clin. Invest.* 81:1297–1301.
(9) "Cellular Injury and Adaptation," in Pathologic Basis of Disease, Cotran et al., eds., WB Saunders, Philadelphia, pp. 1–81 (1989).
(10) Robson, M. C. et al. (1979). *Plastic and Reconstructive Surgery* 63:781–787.
(11) Robson, M. C. et al. (1980). *J. Trauma* 20:722–725
(12) Rockwell, W. B. and Ehrlich, H. P. (1992). *J.Burn Care Rehab* 13:403–406.
(13) Boykin, J. V. et al. (1980). *Plastic Reconstruct. Surgery* 66:191–198.
(14) Erhlich, H. P. (1984). *J. Trauma* 24:311–318.
(15) Erhlich, H. P. (1987). *J. Trauma* 27:420–424.
(16) Mileski, W. et al. (1992). *J. Sugg. Res.* 52:334–339.
(17) Morehouse, J. L. et al. (1986). *Gastroenterol* 91:673–682.
(18) Maejimak, et al. (1984). *Arch, Surg.* 119:166–172.
(19) Czaja, A. J. et al. (1974). *N. Engl. J. Med.* 291:925–929
(20) Seavitt, S. (1967). *Br. J. Surg.* 54:32–41.
(21) Desai, M. H. et al. (1991). *Surgery, Gyn. Obstet.* 172:257–261.
(22) Deitch, E. A. and R. Berg (1987). *J. Burn Rehab.* 8:475–482.
(23) Edmiston, C. E. and R. E. Condon (1991). *Surgery, Gyn. Obstet.* 173:73–83.
(24) Deitch, E. A. (1990). *Arch. Surg.* 125:403–404.
(25) Saadia, R. et al. (1990). *Br. J. Surg.* 77:487–492.
(26) Mainous, M. R. et al. (1991). *Arch. Surg.* 126:33–7.
(27) Vaughan, W. G. et al. (1992). *J. Ped. Surg.* 27:968–973.
(28) Deitch, E. A. et al (1992). *Circ. Shock* 36:206–16.
(29) Fukushima, R. et al. (1992). *Ann. Surg.* 216:438–444.
(30) Tokyay, R. et al. (1992). *J. Trauma* 32:704–713.
(31) Simon, R. H. and Ward, P. A. (1992). In *Inflammation: Basic Principles and Clinical Correlates*, 2d Ed., Galin, J. I. et al., Eds., Raven Press, Ltd., New York, pp. 999–1016.
(32) Araneo, B. A. et al. (1993). *Arch. Surg.* 128: 318–325.
(33) Eich, D. M. et al. (1992). U.S. Pat. No. 5,110,810.
(34) Eich, D. M. et al. (1992). U.S. Pat. No. 5,162,198.
(35) Nestler, J. E. et al. (1990). U.S. Pat. No. 4,920,115.
(36) Kent, S. (1982). *Geriatrics* 37:157–159.
(37) Jackson (1953). *British J. Surg.* 40:588–593.
(38) Ericksson, E. et al. (1980). *Microvascular Res.* 19:374–379.
(39) Anderson, G. L. et al. (1988). *Microvascular Res.* 36:56–63.
(40) Siemionow, M. et al. (*1991*). *Microcirc. Endoth. Lymphatics* 7:183–197.
(41) Siemionow, M. et al. (1993). *J. Hand Surgery* 18A:963–971.
(42) Orlinska, U., (1989). PhD Dissertation: Transforming growth factor β1 and plyamines in monocrotaline-induced pulmonary hypertension. Univ. of Kentucky, School of Pharmacy, Lexington, Ky.
(43) Hawrylowicz, C. H. et al. (1989). *J. Immunol.* 143:4015–4018.

What is claimed is:

1. A method for preventing or reducing adult respiratory distress syndrome (ARDS) in a patient at high risk of ARDS, which comprises administering a therapeutically effective amount of a compound of the formula

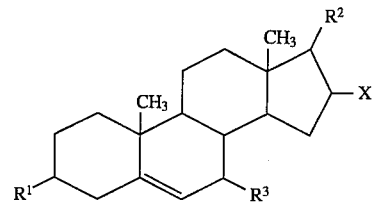

wherein
X is H or halogen;
$R^1$, $R^2$ and $R^3$ are independently =O, —OH, —SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO$_2$R$^5$ or —OPOR$^5$R$^6$;
$R^5$ and $R^6$ are independently —OH, pharmaceutically acceptable esters or pharmaceutically acceptable ethers; and
pharmaceutically acceptable salts, with the proviso that said compound is not of the formula

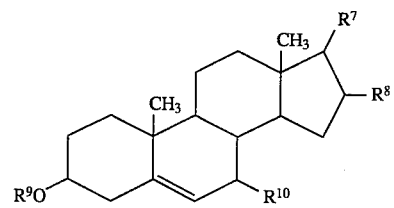

wherein
$R^7$ is =O or OH;
$R^8$ is H or halogen when $R^7$ is =O and $R^8$ is H when $R^7$ is OH;
$R^9$ is H, fatty acid, $C_{1-10}$ alkyl, $C_{1-10}$ alkenyl, $C_{1-10}$ acetylenic, $(Y)_n$-phenyl-$C_{1-5}$-alkyl, $(Y)_n$-phenyl-$C_{1-5}$-alkenyl or —CO—R$^{11}$;
$R^{10}$ is H or OH;
$R^{11}$ is H, fatty acid, $C_{1-10}$ alkyl, $C_{1-10}$ alkenyl, $C_{1-10}$ acetylenic, $(Y)_n$-phenyl-$C_{1-5}$-alkyl or $(Y)_n$-phenyl-$C_{1-5}$alkenyl;
Y is the same or different, and is halogen, $C_{1-4}$ alkyl, $C_{1-4}$ alkenyl, $C_{1-4}$ alkoxy, carboxy, nitro, sulfate, sulfonyl, $C_{1-6}$ carboxylesters or $C_{1-6}$ sulfate esters; and
n is 0, 1, 2 or 3.

2. The method of claim 1, wherein said compound is administered prior to onset of clinical symptoms of ARDS.

3. The method of claim 1, wherein the compound is administered in the amount of 1 to 200 mg/kg.

4. The method of claim 1, wherein the compound is administered in the amount of 2 to 50 mg/kg.

5. The method of claim 1, wherein $R^3$ is OH.

6. The method of claim 1 wherein said compound is dehydroepiandrosterone-3-sulfate (DHEAS).

7. The method of claim 6 wherein the DHEAS is administered intravenously.

8. The method of claim 6 wherein the DHEAS is administered prior to onset of clinical symptoms of ARDS.

9. The method of claim 6 wherein DHEAS is administered orally.

10. The method of claim 6 wherein the DHEAS is administered in the amount of 2–500 mg/kg.

11. The method of claim 6 wherein the DHEAS is administered in the amount of 2–200 mg/kg.

12. The method of claim 6 wherein the DHEAS is administered in the amount of 1–50 mg/kg.

13. The method of claim 6 wherein the DHEAS is administered in the amount of 2–50 mg/kg.

* * * * *

UNITED STATES PATENT AND TRADEMARK OFFICE
CERTIFICATE OF CORRECTION

PATENT NO. : 5,587,369 Page 1 of 1
DATED : December 24, 1996
INVENTOR(S) : Daynes et al.

It is certified that error appears in the above-identified patent and that said Letters Patent is hereby corrected as shown below:

Column 1,
Line 7, the paragraph should read:

-- STATEMENT REGARDING FEDERALLY SPONSORED RESEARCH OR DEVELOPMENT

This invention was made with Government support under Grant No. GM46899 awarded by the National Institutes of Health, Bethesda, Maryland, and under Grant N00014-92-J-1612 awarded by the Department of the Navy. The United States Government has certain rights in the invention. --

Signed and Sealed this

Ninth Day of December, 2003

JAMES E. ROGAN
*Director of the United States Patent and Trademark Office*